United States Patent [19]

Allen et al.

[11] Patent Number: 5,438,017

[45] Date of Patent: Aug. 1, 1995

[54] ASSAYS FOR SULFHYDRYL AMINO ACIDS AND METHYLMALONIC ACID AND THEIR APPLICATION TO DIAGNOSIS OF COBALAMIN DEFICIENCY

[75] Inventors: Robert H. Allen, Englewood; Sally P. Stabler, Denver, both of Colo.

[73] Assignee: The University of Colorado Foundation, Inc., Colo.

[21] Appl. No.: 960,783

[22] Filed: Oct. 14, 1992

Related U.S. Application Data

[63] Continuation of Ser. No. 345,885, May 1, 1989, abandoned.

[51] Int. Cl.[6] .................... G01N 24/00; C12Q 1/00
[52] U.S. Cl. .................... 436/89; 436/174; 436/825; 436/86; 436/120; 436/4; 436/18
[58] Field of Search .................... 435/4, 18; 436/173–174, 8, 86, 120, 825, 89; 514/52, 258

[56] References Cited

U.S. PATENT DOCUMENTS 4,940,658  7/1990  Allen et al. .................... 436/120

OTHER PUBLICATIONS

Information Disclosure Statement submitted in parent application Ser. No. 345,885 dated Nov. 29, 1990.
Declaration under 37 CFR §1.132 dated Nov. 27, 1990, including Exhibit A thereto.
Adams, R. F., "Determination of Amino Acid Profiles in Biological Samples by Gas Chromatography," J. Chromatography (1974) 95:189–212.
Adams, R. F. et al., "Ultramicro GC Determination of Amino Acids Using Glass Open Tubular Columns and a Nitrogen-Selective Detector*", J. Chromatographic Sci. (1977) 15:63–68.
Alberts et al. (1989) Molec. Biol. of the Cell, pp. 583–584, 722–723.
Butler, M. et al., "Amino Acids Attached to Transfer Ribonucleic Acid in vivo," Biochem J. (1975) 150:419–432.
Cancalon, P. and Klingman, J. D., "An Improved Procedure for Preparing the n-Butyl-Trifluoroacetyl Amino Acid Derivatives and Its Application in the Study of Radioactive Amino Acids from Biological Sources," J. Chromatographic Science (1974) 12:349–355.
Chauhan, J. and Darbre, A., "Determination of Urinary Amino Acids by Means of Glass Capillary Gas–Liquid Chromatography with Alkali–Flame Ionisation Detection and Flame Ionisation Detection," J. Chromatography (1982) 227:305–321.
Collins, F. S. and Summer, G. K., "Determination of glutamine and glutamic acid in biological fluids by gas chromatography," J. Chromatography (1978) 145:456–463.
Davis et al. (1990) Microbiology, p. 94.
Desgres, J. et al., "Gas–liquid chromatography of isobutyl ester, N(O)–Heptafluorobutyrate derivatives of amino acids on a glass capillary column for quantitative separation in clinical biology," J. Chromatography (1979) 162:133–152.
Doussin, A. and Bourdon, R., "Determination of various amino acids by gas chromatography. Application to blood microsamples absorbed onto paper," Ann Biol. Clin (Paris) (1972) 30(5):417–426 (abstract only).
Faull, K. F. et al., "Mass spectrometric identification and selected ion monitoring quantitation of γ-amino-butyric acid (GABA) in human lumbar cerebrospinal fluid," J. Neurochemistry (1978) 31:1119–1122.

(List continued on next page.)

*Primary Examiner*—Lyle A. Alexander
*Attorney, Agent, or Firm*—Greenlee and Winner

[57] ABSTRACT

Improved methods for the GC/MS analysis of sulfhydryl amino acids and methylmalonic acids in samples of body fluids are provided. Additionally a method for combined assay of sulfhydryl amino acids particularly total homocysteine and combined creatine/creatinine levels in samples of body fluids provided. The information provided by the methods described is useful in the detection of the presence of cobalamin or folate deficiencies in individuals and in distinguishing between the two deficiencies.

22 Claims, No Drawings

OTHER PUBLICATIONS

Finlayson, P. J. and Christopher, R. K. "Quantitation of fourteen urinary alpha-amino acids using isobutane gas chromatography chemical ionization mass spectrometry with 13CV amino acids as internal standards," Biomed. Mass Spectrom. (1980) 7(10):450–453 (abstract only).

Frank, H. et al., "A new gas chromatographic method for determination of amino acid levels in human serum," Clinica Chimica Acta (1980) 105:201–211.

Frank, H. et al., "Determination of Enantiomer-Labeled Amino Acids in Small Volumes of Blood by Gas Chromatography," Anal. Chem. (1982) 54:715–719.

Gabrys, J. and Konecki, J., "Gas-liquid chromatography of free amino acids in the hyaloplasm of rat cerebral, cerebellar and ocular tissues, and in skeletal and heart muscle," J. Chromatography (1980) 182:147–154.

Gabrys, J. and Konecki, J., "Gas chromatographic analysis of free amino acids in the hyaloplasm of the hypophysis, pineal gland, thyroid gland, spinal cord, thymus and lymph nodes of the cow," J. Chromatography (1981) 222:345–352.

Gehrke, C. W. et al, "Quantitative Amino Acid Analysis by Gas-Liquid Chromatography," J. Agr. Food Chem., (1971) 19:605–618.

Gehrke, C. W. et al., "Quantitative Gas-Liquid Chromatography of Amino Acids in Proteins and Biological Substances", Analytic Biochemistry Laboratories, Inc., Columbia, Mo. (1968) 17–20.

Husek, P. et al., "Contribution to clean-up procedures for serum amino acids," J. Chromatography (1982) 236:493–495.

Kaiser, F. E. et al., "Amino Acid Analysis: Hydrolysis, ion-exchange cleanup, derivatization, and quantitation by gas-liquid chromatography," J. Chromatography (1974) 94:113–133.

Kingston, E. E. and Duffield, A. M., "Plasma Amino Acid Quantitation Using Gas Chromatography Chemical Ionization Mass Spectrometry and $^{13}C$ Amino Acids as Internal Standards," Biomed. Mass Spectrometry (1978) 5(11):621–626.

Labadarios, D. et al., "Gas Chromatographic Analysis of Amino Acids in Physiological Fluids: A Critique," J. Chromatotgraphy (1984) 310:223–231.

Leighton, W. P. et al., "Determination of Erythrocyte Amino Acids by Gas Chromatography," J. Chromatography (1979) 164:427–439.

Lewis, A. M. et al., "Whole-Blood and Plasma Amino Acid Analysis: Gas-Liquid and Cation-Exchange Chromatography Compared," J. Clin. Chem. (1980) 26(2):271–276.

Lindenbaum et al., "Neuropsychiatric Disorders Caused by Cobalamin Deficiency in the Absence of Anemia or Macrocytosis," New Eng. J. Med. (1988) 318:1720–1728.

Mamer and Tjoa, "Trimethylsilylation of Malonate Ester Enols," Clin. Chem. (1973) 19:58–61.

Matthews, D. E. et al., "Determination of Stable Isotopic Enrichment in Individual Plasma Amino Acids by Chemical Ionization Mass Spectrometry," Anal. chem. (1979) 51(1):80–84.

McGregor, R. F. et al., "Determination of Urinary Amino Acids by Gas Chromatography", Clinica Chimica Acta (1973) 48:65–75.

Okano, Y. et al., "Simultaneous Analysis of Pipecolic Acid with Proline in the Brain by Selected Ion-Monitoring Technique," Anal. Biochem. (1981) 117:196–202.

Pellizzari, E. D. et al., "An Evaluation of the Gas Chromatographic Analysis of Plasma Amino Acids," J. Chromatography (1971) 55:281–289.

Pellizzari, E. D., "An Improved Plasma Amino Acid Purification Procedure for Gas-Liquid Chromatography," Anal. Biochem. (1971) 44:312–316.

Rasmussen, K., "Solid-Phase Sample Extraction for Rapid Determination of Methylmalonic Acid in Serum and Urine by a Stable-Isotope-Dilution Method," Clin. Chem. (1989) 35:260–264.

Sanchez, J. and Enjuanes, L., "Gas-liquid Chromatography of Amino Acids in the Blood of Wistar Rats with Walker 256 Carcinoma," Oncology (1971) 25:44–48.

Schulman, J. D. et al., "Gas chromatographic analysis of concentration of amino acids in amniotic fluid from early, middle, and late periods of human gestation," Am. J. Obstet. Gynecol. (1972) 243–249.

Shahrokhi, F. and Gehrke, C. W., "Quantitative Gas-Liquid Chromatography of Sulfur Containing Amino Acids," J. Chromatography (1968) 36:31–41.

Stabler et al., "Quantitation of Total Homocysteine, Total Cysteine, and Methionine in Normal Serum and Urine Using Capillary Gas Chromatography-Mass Spectrometry," Anal. Biochem. (1987) 162:185–196.

(List continued on next page.)

OTHER PUBLICATIONS

Stabler et al., "Elevation of Total Homocysteine in the Serum of Patients with Cobalamin or Folate Deficiency Detected by Capillary Gas Chromatography-Mass Spectrometry," J. Clin. Invest. (1988) 81:466–474.

Stabler et al., "Marked Elevation of Methylmalonic Acid (MMA) in Cerebral Spinal Fluid (CSF) of Patients with Cobalamin (Cbl) Deficiency," Abstract, Meeting of Am. Soc. for Clin. Invest. (1989), Clin. Res. 37:550A.

Stabler, S. P. et al., "Failure to Detect β-Leucine in Human Blood or Leucine 2,3-Aminomutase in Rat Liver Using Capillary Gas Chromatography-Mass Spectrometry," J. Biol. Chem. (1988) 263(12):5581–5588.

Stein, T. P. et al., "Parenteral Nutrition and Human Gastrointestinal Tumor Protein Metabolism," Cancer (1982) 49:1477–1480.

Stryer, L. (1988) Biochemistry, pp. 549, 582–583, 1009 and 1025.

Sweetman, L. et al., "Prenatal Diagnosis of Propionic and Methylmalonic Acidemia by Stable Isotope Dilution Analysis of Methylcitric and Methylmalonic Acids in Amniotic Fluids," Stable Isotopes, Schmidt et al. (eds), Elsevier Scientific, Amsterdam, The Netherlands (1982) pp. 287–293.

Tepper, T. et al., "Loss of amino acids during hemodialysis: quantitative and qualitative investigations," Clin. Nephrology (1978) 10(1):16–20.

Tucker, H. N. and Molinary, S. V., "Gas Chromatography in Diagnostic Biochemistry of Abnormal Valine Metabolism," Clin. Chem. (1973) 19(9):1040–1044.

Williams, K. M. and Halpern, B., "The use of gas chromatography-mass spectrometry for the diagnosis and study of metabolic disorders," Aust. J. Biol. Sci. (1973) 26:831–837.

Zumwalt, R. W. et al., "Gas-Liquid chromatography of amino acids in biological substances," J. Chromatography (1970) 53:171–193.

Zumwalt, R. W. et al., "Applications of a gas-liquid chromatographic method for amino acid analysis," J. Chromatography (1971) 55:267–280.

Norman et al. (1982) Blood 59:1128–1131.

Marcell et al. (1985) Anal. Biochem. 150:58–66.

Stabler et al. (1986) J. Clin. Invest. 77:1606–1612.

Lehninger, Biochemistry, p. 716, ©1975, Worth Publishers, Inc.

Henry, Clinical Diagnosis and Management, pp. 136–136 ©1984, W B Saunders Company.

ASSAYS FOR SULFHYDRYL AMINO ACIDS AND METHYLMALONIC ACID AND THEIR APPLICATION TO DIAGNOSIS OF COBALAMIN DEFICIENCY

The research leading to this invention was, at least in part, funded by U.S. government agencies. The U.S. government has certain rights in this invention.

RELATEDNESS OF THE APPLICATION

The subject application is a continuation of U.S. Ser. No. 345,885, filed May 1, 1989 now abandoned.

FIELD OF THE INVENTION

This invention relates to improved methods for assay of sulfhydryl amino acids and methylmalonic acid in body fluids. The invention further relates to a combined assay of sulfhydryl amino acids, methylmalonic acid and combined creatine/creatinine in body fluids. These improved assays provide information useful in the diagnosis of cobalamin deficiency in warm-blooded animals, particularly humans, and in the distinction of cobalamin deficiency from folic acid deficiency and/or renal insufficiency.

BACKGROUND OF THE INVENTION

Cobalamin (Cbl) or vitamin $B_{12}$ deficiency, usually the result of disruption of the absorption of cobalamin, can lead to life-threatening hematological and neuropsychiatric abnormalities. Accurate and early diagnosis of cobalamin deficiency is important since proper treatment with cobalamin results in complete reversal of the hematologic symptoms. Early diagnosis is especially important in order to avoid potentially incapacitating, irreversible neurologic damage. Administration of exogenous cobalamin always stops the progression of neuropsychiatric abnormalities, almost always leads to significant improvements in such symptoms and frequently leads to their complete correction. Early diagnosis is often difficult since the clinical signs of Cbl deficiency can result from a variety of other disorders. It has generally been taught that Cbl deficiency should be suspected in individuals with significant anemia, displayed for example in decreased hematocrit or hemoglobin, with macrocytic red blood cells (i.e., mean cell volume (MCV) generally greater than 100 fl), or in individuals having the neurologic symptoms of peripheral neuropathy and/or ataxia. Anemia associated with Cbl deficiency has been described as typically severe with hemoglobin $\leq 8$ g % or hematocrit $<25\%$ and the size of the red blood cells is described as greatly increased to levels $>110$ fl. (See, for example, Babior and Bunn (1983) in *Harrison's Principles of Internal Medicine* (Petersdorf et al., eds.) McGraw-Hill Book Co., New York; Lee and Gardner (1984) In *Textbook of Family Practice*, 3rd Ed. (Rakel, ed.) Saunders & Co., Philadelphia).

Cbl deficiency is often difficult to distinguish from folate deficiency because both lead to indistinguishable hematologic abnormalities. It is very important to make this distinction because treatment with the proper vitamin will result in the greatest improvement in hematologic symptoms and the neuropsychiatric abnormalities associated with Cbl deficiency are only corrected by cobalamin treatment. Furthermore, the incorrect treatment of Cbl deficiency with folate can be dangerous in that folate treatment may improve some, or all, of the hematologic abnormalities thereby disguising the presence of Cbl deficiency and delaying timely treatment with cobalamin. As noted above, delay in cobalamin treatment can in some cases result in irreversible neurologic damage.

The serum cobalamin assay has been essentially the only laboratory assay generally available for use in determining if a patient is Cbl deficient. Presently preferred cobalamin assays are radiodilution assays which use pure or purified intrinsic factor as the binding protein (see: Kolhouse et al. (1978) *New Eng. J. Med.* 299:785–792). This assay has been criticized as frequently giving low Cbl values in patients who lack any evidence of Cbl deficiency. It has been suggested (Schilling et al. (1983) *clin. Chem.* 29:582–583) that this assay may frequently give false positives showing low serum Cbl levels in individuals who are not Cbl deficient.

It has long been known that methylmalonic acid (MMA) is excreted in increased amounts in the urine of most patients with Cbl deficiency (see, for example, Cox and White (1962) *Lancet* ii:853–856; Norman et al. (1982) *Blood* 59:1128–1131). In Cbl deficiency, reduced levels of adenosyl-Cbl result in decreased activity of L-methylmalonyl-coenzyme A (CoA) mutase and a concomitant increase in intracellular levels of L-methylmalonyl-CoA. D-methylmalonyl-CoA, resulting from transformation of the L-isomer by D,L-methylmalonyl-CoA racemase (Stabler et al. (1985) *Arch. Biochem. Biophys.* 241:252–264), is cleaved to CoA and MMA by D-methylmalonyl-CoA hydrolase which has been recently characterized (Kovachy et al. (1983) *J. Biol. Chem.* 228:11415–11421). MMA is then released into blood in unknown amounts and is excreted in the urine. About 70% of the MMA in blood is metabolized to unknown products via as yet undefined pathways and only about 30% is excreted in the urine.

Recently, Marcell et al. (1985) *Anal. Biochem.* 158:58–66 reported that MMA in the serum and urine of normal subjects ranged from 19–76 ng/ml and 270–7190 ng/ml, respectively. Stabler et al. a. (1986) *J. Clin. Invest.* 77:1606–1612 reported that serum MMA levels of clinically confirmed Cbl deficient patients ranged from 55 to 22,300 ng/ml, with 69 of 73 of such patients having serum MMA levels above the normal range. It was also reported that there was a positive correlation between serum MMA levels and the presence of neurologic abnormalities in these patients. Lindenbaum et al. (1988) *New Eng. J. Med.* 318:1720–1728 reported that serum MMA levels were elevated above normal levels in 36 of 37 Cbl deficient patients who displayed neuropsychiatric abnormalities in the absence of anemia or other severe hematologic abnormalities. Further, it was suggested that high serum MMA levels which return to normal after cobalamin therapy provide a useful confirmation of the presence of Cbl deficiency.

Stabler et al. (1989) "Marked Elevation of Methylmalonic Acid in Cerebral Spinal Fluid of Patients with Cobalamin Deficiency" Abstract for the meeting of the American Society for Clinical Investigation (Clinical Research (1989) 37:550A), have very recently determined MMA levels in cerebral spinal fluid (CSF) of normal (non-Cbl deficient) and Cbl deficient patients. It was found that MMA levels in CSF are significantly elevated in patients with confirmed Cbl deficiency. It was also found that in Cbl deficient patients, MMA CSF levels were elevated to a greater degree than were MMA serum levels. Further, in several patients having high serum MMA due to renal failure, MMA levels in CSF were within the normal range or only slightly elevated.

The diagnosis of folate deficiency has, likewise, been almost entirely dependent on the demonstration of low serum levels of the vitamin in patients with supportive clinical and laboratory findings. Thus, the most widely utilized and recommended assays for diagnosing and distinguishing Cbl and folate deficiency have been assays of serum levels of the vitamins. Like Cbl deficiency, the diagnosis of folate deficiency can be problematic. For instance, after acute dietary deprivation, serum folate levels may be decreased, even though tissue folate levels are adequate (Herbert (1962) *Arch. Intern. Med.* 110:649–652). In the setting of chronic alcoholism, the laboratory features of megaloblastic anemia due to folate deficiency may be confused by concurrent illness. Serum and red blood cell folate levels may be normal in patients with alcoholism and megaloblastic anemia.

The sulfhydryl amino acids are metabolized by a complex set of pathways (see: Stabler et al. (1988) *J. clin. Invest.* 81:466–474) in some of which cobalamin and folic acid are vital cofactors. Methylation of homocysteine (Hcys) to form methionine which is catalyzed by methionine synthetase requires methylcobalamin (Me-Cbl). The methyl group is donated by $N^5$-methyltetrahydrofolate, which is converted to tetrahydrofolate (THF). Thus, both cobalamin and folate are cofactors in sulfhydryl amino acid metabolism and cobalamin, but not folate, is a cofactor in methylmalonyl-CoA metabolism. Elevated serum and urine levels of homocystine and/or methionine have been reported in children having inherited defects due to inability to synthesize the cofactors $N^5$-methyltetrahydrofolate or Me-cobalamin or to defects in methionine synthetase (see: Mudd (1974) in *Heritable Disorders of Amino Acid Metabolism: Patterns of Clinical Expression and Genetic Variation* (Nyhan, ed.) John Wiley & Son, New York).

Stabler et al. (1988) supra reports that elevated levels of serum total homocysteine correlate with the presence of either Cbl deficiency or folate deficiency. Most patients with confirmed Cbl deficiency (77 of 78) or folate deficiency (18 of 19) were found to have total serum Hcys levels above the normal range of 7–22 $\mu$mol/liter. This reference also reports that measurement of both serum MMA and total Hcys levels can be used to distinguish between Cbl and folate deficiency, since most patients having only folate deficiency have normal serum MMA levels.

Marcell et al. (1985) supra; Stabler et al. (1987) *Anal. Biochem.* 162:185–196; and Allen et al. U.S. Pat. application Ser. No. 933,553 describe gas chromatography/mass spectrometry selected ion monitoring (GC/MS-SIM) methods for quantitating serum and urine levels of total homocysteine and methylmalonic acid. The assay methods described, particularly that for MMA, require multistep, time-consuming laborious sample preparation due, for the most part, to the low concentration of MMA and Hcys in serum and to the presence in serum of compounds which interfere with quantitation. Homocysteine analysis in body fluids is further complicated since homocysteine readily forms disulfide bonds with itself, other sulfhydryl amino acids (i.e., cysteine) and free sulfhydryl groups in proteins present in such fluids. Separate, different sample preparations are required for the analysis of the two compounds. Development of improved rapid and reproducible assays for serum MMA and Hcys would be desirable. Improvements that would allow combined assay of MMA and homocysteine and which would be amenable to automation of the assay methods would be particularly desirable.

Elevation of MMA levels in urine and serum can result from renal insufficiency. Similarly, Hcys has been reported to be present in small amounts, compared to undetectable levels in normal serum, in serum of patients with renal insufficiency. Renal insufficiency is known to correlate with the level of creatinine in serum. A number of methods for the assay of creatinine are known and the most widely employed assays are based on colorimetric detection. A determination of the presence of renal insufficiency, for example, by assay of creatinine would be useful additional information in the diagnosis of Cbl and folate deficiency. Adaptation and combination of a quantitative assay for creatinine with GC/MS methods of quantitation of MMA and Hcys would be of significant practical utility.

SUMMARY OF THE INVENTION

The present invention provides improved methods for assaying sulfhydryl amino acids, such as homocysteine and cysteine, and methylmalonic acid in body fluids. The determination of the levels of certain of these metabolites, homocysteine and methylmalonic acid, in body fluids is useful in the diagnosis of cobalamin or folate deficiency.

The improvements described herein result in more rapid, more reproducible and more sensitive analysis of sulfhydryl amino acids and methylmalonic acid compared to previously described methods.

Known GC/MS methods for analysis of sulfhydryl amino acids, including homocysteine, in biological tissues and fluids involve the following general steps: addition of a known amount of an internal reference standard for the sulfhydryl amino acid(s) to be analyzed (for example, isotopically labelled sulfhydryl amino acid) to samples; addition of reducing agent to the sample to insure randomization of any endogenous or added reference sulfhydryl amino acids present in the sample; optional addition of an alkylating agent to prevent dimerization of the sulfhydryl amino acids; partial purification of the samples to remove components that interfere with the subsequent capillary gas chromatography; derivatization of the samples, for example with silating agents; and analysis of the derivatized samples in a gas chromatograph/mass spectrometer to determine the amount of endogenous sulfhydryl amino acid present in the sample. It has been discovered that samples of body fluids assayed for sulfhydryl amino acids can be sufficiently purified for quantitative analysis of those acids by GC/MS in a single step chromatographic extraction procedure. The present invention provides an improvement for sulfhydryl amino acid sample purification. The improved method utilizes addition of alkylating agent after the addition of the reducing agent in order to prevent recombination of sulfhydryl amino acids in the sample. After alkylation of the free SH groups in the sample, the sample is purified in a single ion exchange chromatographic extraction on either a cation or anion exchange column, with cation exchange purification being preferred. A cation exchange resin in the hydrogen or ammonium ion form is preferred for this application with the hydrogen ion form being more preferred. An anion exchange resin in a weaker counter-ion form, such as hydroxide or acetate ion form, is preferred in this application, with the acetate ion form being more preferred. For example, an anion exchange resin that is strongly basic such as AGMP-1 (acetate form) (Biorad, Richmond, Calif.), or resins functionally equivalent thereto, can be employed. When cation exchange extraction is used, the sample is eluted with a solution of aqueous or organic base. It is preferred that the eluting solvent is volatile, such as a basic methanol solution. When anion exchange is used, the sample is eluted with a solution of aqueous or organic acid, preferably an acidic solution of methanol, which is a volatile solvent. For use with an anion exchange resin in the acetate form, an acidified methanolic solution is preferred, and a solution of 1N HCl in methanol is most preferred. Moreover, it is preferred that in performing the single ion exchange chromatographic extraction, the washing and elution steps are allowed to flow under gravity.

In a specific embodiment, serum or plasma samples are prepared for GC/MS analysis of Hcys by addition of a known amount of the internal standard, e.g. deuterated homocystine, followed sequentially by: addition of the reducing agent, dithiothreitol in $H_3BO_3$ (pH 10); addition of the alkylating agent, iodoacetamide; partial sample purification by column chromatography employing a strong acid cation exchange resin, such as AG50WX8 resin (hydrogen form) (Biorad, Richmond, Calif.), washing sequentially with water and methanol and eluting with a basic aqueous methanol solution, such as a 4N $NH_4OH$ methanol solution; and derivatization of the samples with the silating agent, N-methyl-N-(t-butyldimethyl-silyl)trifluoroacetamide (MTBSTFA). This specific method for analysis of Hcys can also be employed with samples of cerebral spinal fluid (CSF) and urine. Total cysteine, methionine and other amino acids can also be determined in this analysis.

Known GC/MS methods for analysis of methylmalonic acid, in biological tissues and fluids involve the following general steps: addition of a known amount of an internal reference standard for methylmalonic acid, for example, deuterated methylmalonic acid to samples; partial purification of the samples to remove components that interfere with the subsequent capillary gas chromatography; derivatization of the samples, for example with silating agents; and analysis of the derivatized samples in a gas chromatograph/mass spectrometer to determine the amount of endogenous methylmalonic acid present in the sample. It has been discovered that body fluid samples assayed for methylmalonic acid can be sufficiently purified for quantitative analysis of MMA by GC/MS in a single step chromatographic extraction procedure. The present invention provides alternative improvements for methylmalonic acid sample purification. Both improved methods require only a single column chromatographic procedure, and are greatly simplified compared to previously described methods of MMA sample purification. One improved method employs a single step of silica gel chromatographic extraction in which the sample is extracted with an appropriate organic solvent, such as ether; the organic extract is then applied to a silica gel column, the column is then washed with methanol and the sample is eluted from the column with a solution of base in methanol, such as 4N $NH_4OH$ in methanol. A second improved method employs a single step of chromatographic extraction employing a macroporous strongly basic anion exchange resin, washing the column sequentially with water, methanol and a solution of a weak counter-ion in methanol, such as acetic acid, specifically a solution of 0.01–0.1N acetic acid in methanol, and eluting the sample from the column with a solution of a strong counter-ion in methanol, such as HCl in methanol, specifically with a solution of about 0.1–1.0N HCl in methanol.

In specific embodiments, serum or plasma samples are prepared for GC/MS analysis of MMA by addition of a known amount of the internal standard, deuterated MMA, followed sequentially by: partial sample purification by column chromatography employing either silica gel or anion exchange resin, as described above; and derivatization of the samples with the silating agent, MTBSTFA. Sample purification employing the macroporous strongly basic anion exchange resin is preferred. Also, sample purification employing a strongly basic anion exchange resin in the chloride form is a preferred method. These methods can also be employed for the quantitation of MMA in CSF and urine. Succinic acid can also be determined in this analysis.

The improved methods for sulfhydryl amino acid and MMA analysis by GC/MS can be combined to decrease the number of manipulations required. In such a combined assay a known amount of sulfhydryl amino acid internal standard and MMA internal standard are added in a single addition to a single sample, after which the sample is divided into two portions: an Hcys sample portion and a MMA sample portion. The Hcys portion and the MMA portions are then treated, purified and derivatized by the improved methods described above.

The improved methods described herein can also be combined with a GC/MS determination of combined creatine/creatinine in a sample of body fluid. A known amount of an internal standard, i.e. isotopically labelled creatine or creatinine, is introduced into a sample, the samples are treated, purified and derivatized as described herein for sulfhydryl amino acid samples and analyzed for combined creatine/creatinine by GC/MS techniques. Combined creatine/creatinine can be quantitated using the same capillary gas chromatographic procedure, and the same column and temperature conditions, as employed for quantitation of Hcys and cysteine.

The improved methods described herein are amenable to automation using automated pipetting systems and GC/MS automated injector systems.

The improved methods described herein as applied to the assay of Hcys and MMA are useful for detecting Cbl or folate deficiency and distinguishing therebetween in warm-blooded animals, particularly humans.

It has been discovered that combined creatine/creatinine levels in urine and serum as measured by the GC/MS method described herein directly correlate with conventional colorimetric or enzymatic assays of creatinine in urine and serum. The GC/MS assay of creatine/creatinine can be employed to assess urine dilution in order to correct the assay of other metabolites for urine dilution, and can be employed with serum samples to detect the presence of renal insufficiency or renal failure. Thus, the combined method, described herein, for assaying Hcys, MMA and combined creatine/creatinine is useful not only for detecting Cbl or folate deficiency and distinguishing between the two deficiencies in individuals, but also for correcting MMA and Hcys concentrations assayed in urine for differences in urine dilution between individuals; and for distinguishing the presence of renal insufficiency or failure in those individuals.

DETAILED DESCRIPTION OF THE INVENTION

The measurement of sulfhydryl amino acids and methylmalonic acid in body fluids, particularly in serum, is complicated by the low concentrations of these compounds present and the presence in samples of other compounds which interfere with quantitation. The measurement of sulfhydryl amino acids is further complicated by the tendency of these compounds to bind to free SH groups in proteins present in the sample and to dimerize with other sulfhydryl amino acids present in the sample. Addition of a reducing agent to samples is required to release protein bound sulfhydryl amino acids and dissociate dimers. After initial reduction, however, the sulfhydryl amino acids can reform new disulfides, so the quantitation of these compounds must take this dimerization into account.

Stabler et al. (1987) *Anal. Biochem.* 62:185-196 describe a capillary GC/MS method for analysis of total homocysteine and total cysteine in serum and urine. This assay measures total homocysteine and total cysteine which refers to the total amount of homocysteine or cysteine present in the sample in free or complexed forms. In this method, internal standards are added to samples after which a reducing agent is added to release protein bound homocysteine and cysteine and randomize labelled (reference) and unlabelled homocysteine and cysteine. The internal reference standard is any suitable compound which will behave identically to the endogenous target compound during sample preparation, but which can be distinguished from the target compound by mass spectrometric analysis. Since the reference standard and endogenous target compound are randomized, the ratio of the endogenous compound to internal standard, in any form they occur (i.e., dimer or mixed dimer) will be constant and can be determined by mass spectrometric analysis. The amount of endogenous target can be determined from this ratio and the amount of internal reference standard added. Stable isotopically labelled sulfhydryl amino acids are suitable internal reference standards.

In this method, particularly for serum samples, it was necessary to partially purify samples prior to GC/MS analysis to remove compounds in the sample that interfered with quantitation. A two step column anion exchange extraction purification procedure was utilized in which acidified sample was applied to a cation-exchange column, the column was washed with water and the amino acids were eluted from the column with aqueous base (8N $N_4OH$). Eluate from the cation exchange column was then applied directly to an anion exchange column which was then washed with water and the amino acids were eluted with aqueous acid (0.1M HCl). Eluted samples were dried and derivatized to t-butyl dimethylsilyl esters with MTBSTFA. The derivatized samples were then analyzed by GC/MS in the single ion monitoring mode.

Marcell et al. (1985) *Anal. Biochem.* 50:58-66 describe a method for analysis of MMA in normal serum and urine using capillary GC/MS. In this method, urine and serum samples subjected to multi-step purification prior to derivatization and analysis. The purification procedure is particularly important for the analysis of serum samples due to the presence of compounds which interfere with quantitation. Samples are first made alkaline (pH 12), extracted with ether and the extract discarded, the samples are then acidified (pH 1) and extracted a second time with ether. The second extract is evaporated, and an aqueous solution of the sample residue subjected to anion-exchange high-performance liquid chromatography (HPLC). The mobile phase employed was 0.05M $KH_2PO_4$-$H_3PO_4$, pH 2.0 and 2-ml fractions were collected at a flow rate of 2 ml/min, with MMA and succinic acid eluting in fractions 3-5. The combined HPLC fractions were pooled, acidified to pH 1 and extracted with ether. The residue of the ether extract, after removal of solvent, was derivatized using MTBSTFA. Finally the derivatized samples were extracted with hexane, the hexane extracts were concentrated and injected into a GC/MS for analysis. This method and the method described in Stabler et al. are also disclosed in Allen et al., U.S. patent application Ser. No. 933,553, filed Nov. 20, 1986.

The methods described herein are improvements of the foregoing methods. These improvements are in the main the result of efforts to improve the speed and efficiency of these assays by minimizing the number of steps required, particularly during sample preparation. These efforts have also been directed to developing sample purification procedures which are amenable to automation and batch processing of samples, for example, through the use of automated pipetting equipment. Specifically sample purification in the sulfhydryl amino acid and MMA assays have been improved so that they involve single chromatographic column extraction procedure. Such column extraction procedures require application of the sample to a column, followed by one or more steps of washing the column to remove unwanted components after which the partially purified sample is eluted from the column by addition of a small amount of appropriate solvent. Certain of the washing steps can be critical to remove sample components which interfere with the GC/MS quantitation of the target compounds. The column chromatography procedures of the improved methods described herein are designated chromatographic extractions to distinguish them from other liquid chromatographic fractionation procedures in which, during elutions, multiple fractions are collected and desired components are isolated in only certain of the fractions. Fractionation methods are less rapid than extraction methods, may require monitoring of the content of the fractions and, while amenable to automation are not easily adapted to batch processing of samples. In the column extraction procedures of the present invention, all washing and sample elution are simple gravity elutions which do not require application of vacuum, for example, to speed or control the rate of solvent flow in the columns. It was not found to be necessary in the procedures of the present invention to control column flow rate, or to prevent columns from running dry. Samples can be dried completely, derivatized with appropriate silyl groups and injected directly into the GC/MS for analysis. No sample manipulations are required after derivatization.

In the case of the sulfhydryl amino acid assay, two steps of ion exchange extraction have been replaced with a single step using a cation or anion exchange column. Samples of appropriate pH are applied to the column, which is then washed with water and methanol. Elution of the sulfhydryl amino acids is achieved by addition of a solution of base in methanol, specifically ammonium hydroxide in methanol or acid in methanol.

In the case of MMA, two improved methods of purification have been discovered. The first involves a single ether extraction of the sample followed by chromatographic extraction on a silica gel column, which is washed with methanol and the sample is eluted with a solution of base in methanol, specifically ammonium hydroxide in methanol. The second, and preferred method of MMA sample purification does not require initial extraction into organic medium: diluted samples are directly applied to an anion exchange column containing a strongly basic anion exchange resin, which is washed with water, methanol and a volatile acidic solution of a weak counter-ion such as a dilute (about 0.01–0.1N) solution of acetic acid in methanol. Sample is eluted with an acid solution of a more potent counter-ion in methanol such as HCl in methanol at concentrations between about 0.1 to 1.0N. The final wash with the solution of weak counter-ion, i.e. acetic acid in methanol, was found to be important for the removal of components that interfered with quantitation of the t-butyldimethylsilyl derivatives of MMA by GC/MS. The improvements to the MMA assay not only decrease the time required to perform the assays, but were found to increase the efficiency of recovery of the MMA in the samples compared to the methods described in Allen et al. U.S. Ser. No. 933,553.

Due to the low levels of sulfhydryl amino acids and MMA encountered in samples, particularly serum samples, it was important to retain sensitivity of the analysis while implementing a simplified purification. The improved methods achieve the desired simplification and retain assay sensitivity.

Sweetman et al. (1982) In *Stable Isotopes* (Schmidt et al., eds.) Elsevier Scientific, Amsterdam, The Netherlands, pp. 287–293 have described an analysis of MMA in amniotic fluid utilizing a deuterated internal standard with liquid partition chromatography derivatization with diazomethane and chemical ionization GC/MS. The reference refers to a method of sample preparation in which acidified (with 0.5N $H_2SO_4$) samples of concentrated amniotic fluid containing MMA internal standard are absorbed onto a silicic acid column which was prepared with silicic acid hydrated with $H_2SO_4$ and rinsed with % 9 (v/v) 2-methyl-2-butanol/chloroform. Samples were eluted from the column at 2.5 ml/min with the 2-methyl-2-butanol/chloroform solvent and fractions between 52.5–75 ml, containing MMA, were collected. Samples were acidified, dried and methylated with diazomethane reagent in a methanol/ether solution. This method is distinct from the method for MMA purification described in that they employ a chromatographic fractionation method rather the extraction methods of the present invention.

The improved sulfhydryl amino acid assay described herein requires addition of an alkylating agent, such as iodoacetamide, after the reduction step in order to prevent redimerization of the sulfhydryl amino acids in the sample. The partial redimerization of the sulfhydryl amino acids in the sample does not prevent quantitation of these acids, because of the use of internal standards. The use of the alkylating agent, however, maximizes the monomer form of the sulfhydryl amino acid, which is the preferred forms for MS analysis, in the sample and thus maximizes sensitivity of the assay. The use of alkylating agents such as iodoacetamide was an optional feature of the method of Allen et al. U.S. Ser. No. 933,553. The present work, however, has demonstrated that the SH group alkylation step can be successfully combined with the improved one-step cation exchange extraction purification, derivatization with t-butyldimethylsilyl groups and GC/MS separation and quantitation of the derivatized sulfhydryl amino acids. Iodopropane was also found to work for aklylation of SH groups; however, iodoacetamide was preferred. In contrast, and unexpectedly, iodoacetate was not suitable for use in the present application. It is believed that the silyl derivatives of the sulfhydryl acids treated with iodoacetate are unstable.

Rasmussen (1989) *Clin. Chem.* 35:260–264 refers to the use of a single column anion-exchange extraction for MMA serum and urine sample preparation for use with GC/MS analysis. A strong anion exchange extraction column, Bond Elute (Trademark) SAX containing a sorbent described as trimethylaminopropyl bonded to silica in the chloride form manufactured by Analytichem International (Harbor City, Calif. ) in which the sorbent ion was changed to formate was employed. In the sample purification described: columns are prepared by sequential washing with 1M formic acid, methanol and water; application of the sample to the column; washing of the column with water; and elution of retained acids with 18M formic acid. It is stated in this reference that all column washings and extraction steps should be performed under reduced pressure such that the solutions are aspirated through the column at a flow rate of 1 ml/min. It is also stated that the columns should not be allowed to run dry prior to sample application. The sample preparation described did not employ derivatization with silyl groups. It is specifically stated that "the t-butyldimethylsilyl derivative is unsatisfactory for quantitative work because of interference during GC from co-eluting compounds in serum." A similar problem with the use of silyl derivatives is purported to be described in Mamer and Tjoa (1973) *Clin. Chem.* 19:58–61. In place of silyl group derivatization, the samples are treated with cyclohexanol/HCl. It is noted that cyclohexanol must be evaporated, and the derivatized samples taken "to near dryness" with the residue subsequential taken up in methanol. Rasmussen also notes that strong anion-exchange columns in hydrogen, chloride or acetate ion form using sulfuric acid as the elution solvent had been used to extract organic acids from plasma and serum and implies that these procedures were not satisfactory for GC analysis, particularly of serum compounds, due to the presence of interfering compounds in column eluate. The MMA anion exchange extraction purification method of the present invention is distinct from those of Rasmussen (1989) Supra, in that the latter employs different washing and elution steps, requires cumbersome use of vacuum aspiration of columns and control of column flow rates. Furthermore, the Rasmussen method is described as not compatible with the use of silyl group derivatization, specifically with derivatization with t-butyldimethylsilyl groups.

The improved assays for sulfhydryl amino acids and MMA can be combined for analysis of samples. When the assays are combined, known amounts of internal reference standards, for the sulfhydryl amino acids and MMA are added together to a single sample, after which the sample is divided into two portions: an Hcys portion and a MMA portion. These portions are then treated, purified, derivatized and assayed as described for the individual improved assays.

It has been discovered that the body fluid samples prepared for sulfhydryl amino acid analysis can also be analyzed simultaneous, using the same GC/MS procedures, for combined creatine/creatinine. Creatine and creatinine are readily interconverted chemically.

Under the conditions employed for the preparation of sulfhydryl amino acid samples, creatine in the samples is quantitatively converted to creatinine. The assay is adapted for analysis of combined creatine/creatinine in addition to sulfhydryl amino acids simply by addition of an internal reference standard for creatine or creatinine, such as deuterated creatine, prior to reduction, alkylation and purification of the samples. The creatinine in the purified samples is derivatized, and the derivatives can be separated and quantitated in the same procedure and at the same time as any sulfhydryl amino acids also present in the sample. The values of combined creatine/creatinine obtained by the described GC/MS assay have been found to correlate well with values obtained using conventional colorimetric methods which specifically assay creatinine. Thus, the described methods can be used to determine if creatine/creatinine levels in samples are within the normal range or elevated.

The information provided by the improved methods described herein can be employed to detect the presence of cobalamin or folate deficiency in warm-blooded animals, particularly in humans. Stabler et al. (1986) *J. clin. Invest.* supra and Stabler et al. (1988) *J. Clin. Invest.* supra have demonstrated the usefulness of Hcys and MMA measurements in the diagnosis of these deficiencies and in distinguishing between the two conditions. The additional information provided by simultaneous determination of combined creatine/creatinine in samples of serum of patients is valuable in distinguishing whether the elevation of the metabolites in a sample is due to renal insufficiency or failure. Additional information obtained from creatine/creatinine assays is useful for determining urine dilution and for expressing urine metabolite concentrations relative to urine creatine/creatinine concentrations.

The invention is further illustrated and exemplified by the following non-limiting examples.

EXAMPLES

EXAMPLE 1

Representative Improved GC/MS Assay for Total Homocysteine in Serum

A volume of 50 $\mu$l of an aqueous solution containing a known amount of the internal standard (i.e., 100–200 ng of D,L-[3,3,3', 3', 4,4,4', 4'-$^2$H$_8$]-homocystine) is mixed well with 40 $\mu$l of a serum sample. If less than 40 $\mu$l of sample is used the difference is made up with 0.15M NaCl. A volume of 55 $\mu$l of a reducing agent, H$_3$BO$_3$-DTT (dithiothreitol) solution (0.11 ml 0.5M H$_3$BO$_3$, pH 10+0.55 ml DDT 20 mg/ml in H$_2$O+0.55 ml H$_2$O) is then added to the samples and they are mixed well. The samples are covered and placed at 40° C. for 30 min. Iodoacetamide (40 $\mu$l of 62.5 mg/ml solution in water) is then added to the samples and they are mixed, covered and returned to 40° C. for another 30 min. The samples are then diluted by addition of 1 ml of H$_2$O vortexed. The entire sample is then applied to a cation exchange column which can be either a custom-made, prepacked cation exchange column, or a column prepared by addition of about 0.2 ml cation exchange resin AG50WX8 100–200 mesh hydrogen form (Bio-Rad, Richmond, Calif.). Custom prepacked columns were made to the following specifications by Analytichem International (Harbor City, Calif.): 4 ml polypropylene reservoir equipped with two 70 micron polyethylene frits and containing 50 mg of dry AGMP 50 50–100 mesh (hydrogen form) cation exchange resin (Biorad, Richmond, Calif.). Prepacked columns are prewashed with 3 ml of methanol. AG50WX8 resin used in column chromatography is prepared as a pourable slurry by suspending the dry resin in water. AG50WX8 columns are prewashed with about 1.5 ml of H$_2$O and allowed to stand at room temperature before use. After the sample is applied, both columns are washed sequentially with 3×3 ml H$_2$O and 3 ml of methanol. The column washes are discarded. The sample is eluted from the column with 2 ×0.5 ml 4N NH$_4$OH in methanol (prepared by mixing 125 ml of 16N N$_4$OH (28–30%) and 375 ml of methanol) and the eluates are collected. If a AG50WX8 resin column is employed, an initial careful addition of 100 $\mu$l of 4N NH$_4$OH in methanol near the top of the column avoiding disturbance of the resin bed precedes the 0.5 ml elutions. The eluted samples are dried completely with heat under vacuum (e.g., about 1 hr. in a drying centrifuge). Residues are taken up in 300 $\mu$l of methanol, transferred to autosampler vials and again dried completely with heat (about 45 min.). The samples are derivatized by addition of (20 $\mu$l acetonitrile+10 $\mu$l MTBSTFA. The samples are sealed with Teflon-silicone septa caps, vortexed and placed at 40° C. for 30 min. Samples can be analyzed for total homocysteine within several days or stored at −20° C. for later assay.

About 2 $\mu$l of the derivatized sample is injected onto the capillary column of a Hewlett-Packard (Palo Alto, Calif.) 5890 gas chromatograph-mass spectrometer (GC/MS) via a 7673a autosampler injector. Sample resolution is achieved on a Durabond DB-1 fused silica capillary column (30m×0.25 mm i.d., 0.25 $\mu$m film thickness) from J & W Scientific, Inc. (Rancho Cordova, Calif.). The GC/MS is operated under standard autotune conditions with an injection port temperature of 250° C. and a column head pressure of 15 psi. The capillary column is equilibrated at 140° C. and approximately 10 min after sample injection is increased to 300° C. at a rate of 30° C./min.

Data are collected from 5.0 to 9.6 min. using the selected ion monitoring mode. The [M-57]+ ions homocysteine monomer, m/z 477.3; [3,3,4,4-$^2$H$_4$] homocysteine monomer, m/z 481.3 are monitored using a 10 msec dwell time for each. Total homocysteine is quantitated by dividing the integrated area or the m/z 477.3 peak that elutes at approximately 9.2 min. (the exact elution times are determined with standards) by the integrated area of the m/z 481.3 peak that elutes at the same time, and then multiplying by the amount of internal standard, as labelled homocysteine monomer that was added to each sample.

If desired, total cysteine and/or methionine and/or other amino acids in the sample can be measured concurrently with total homocysteine. Quantitation of total cysteine and methionine, for example, requires initial addition of appropriate internal standards, i.e. 1,000 to 2,000 ng of D,L-[3,3,3', 3'-$^2$H$_4$] cystine and 500 to 1,000 ng of L-[methyl-$^2$H$_3$] methionine to the samples. Samples are treated and chromatography is performed as for assay of Hcys. In addition to the homocysteine [M-57]+, the following [M-57]+ ions are monitored: cysteine monomer m/z 463.3; [3,3-$^2$H$_2$] cysteine monomer, m/z 465.3; methionine, m/z 320.2 and [methyl-$^2$H$_3$] methionine, m/z 323.2. Derivatized cysteine monomer and methionine peaks elute at 8.6 and 5.8 min., respectively. Total cysteine and methionine are quantitated in a manner analogous to that described above for homocysteine.

The integrated areas for any internal standard peaks are corrected for the amounts contributed to them by endogenous total homocysteine, cysteine and methionine as a result of naturally-occurring isotope abundance. These corrections are determined with unenriched homocysteine, cysteine and methionine.

The molecular weight of homocysteine and homocystine are 135 and 268, respectively. During sample preparation, the free sulfhydryl group of homocysteine is alkylated with iodoacetamide. The alkylated homocysteine has a molecular weight of 192. The molecular weight of the t-butyldimethylsilyl derivative of alkylated homocysteine is $192+(3\times114)$ (for three silyl groups bonded to the COOH and $NH_2$ groups), or 534. The mass spectrum of the derivatized alkylated homocysteine contained a major peak at [M-57]+ due to loss of $C_4H_9$. For comparison, the molecular weight of derivatized homocystine is 724 (with four silyl groups). The mass spectrum of the homocystine derivative contains a major peak at [m/z]+,362, and no [M-57]+ peak is observed The [M-57]+ peaks, noted above, are also the major peaks observed in the mass spectra of derivatized cysteine and methionine.

L-homocysteine and L-cysteine were purchased from Sigma Chemical Co. (St. Louis, Miss.); MTBSTFA was obtained from Pierce Chemical Co. (Rockford, Ill.); D,L-[3,3,3′, 3′, 4,4,4′, 4′-$^2H_8$] homocystine (98.4%) was obtained by custom synthesis from Merck, Sharp and Dohme.

EXAMPLE 2

Representative Improved GC/MS Assay for Methylmalonic Acid in Serum

A volume of 50 μl of $H_2O$ containing known amounts of internal standards, i.e. 100–200 ng of [methyl-$^2H_3$]MMA and 1000–2000 ng of [1,4-$^{13}C_2$]succinic acid, is added to 400 μl of serum. The pH of the samples is then adjusted to about 1 by adding 1 ml of 0.6N HCl and the acidified samples are mixed. The samples are then extracted with diethyl ether by addition of 9 ml of ether, followed by vortexing (15 min). The ether layer (leaving about 1 cm of ether on top of the water layer) is collected and applied to a polypropylene column ($0.8\times4.0$ cm) containing 0.8–1.0 ml of silica gel (70-230mesh, Cat. No. S-2509, Sigma Chemical Co, St. Louis, Mo.) which was prewashed and equilibrated with ether. After the sample is applied, the column is washed ($3\times3$ ml) with methanol and the washes discarded. Sample is eluted from the column with 2 ml of 4N $N_4OH$ in methanol into a $12\times75$ mm culture tube. Methanol is removed (to dryness) from the samples in a Speed Vac vacuum concentrator (Savant Instruments, Inc. Hicksville, N.Y.). Sample residue is taken up in 300 μl of methanol and transferred to a polypropylene autosampler vial. Methanol is removed (to dryness) from the samples in the vacuum concentrator. Dicarboxylic acids in the samples are then derivatized to t-butyldimethylsilyl esters by adding 20μl of acetonitrile and 10 μl of MTBSTFA to each vial. The vials are sealed with aluminum-seal, Teflon-silicone septa caps, vortexed and allowed to stand at 40° C. for 30 min.

About 2 μl of the derivatized sample is injected onto the capillary column of a Hewlett-Packard (Palo Alto, Calif.) 5890 gas chromatograph-mass spectrometer (GC/MS) via a 7673a autosampler injector. Sample resolution is achieved on a Durabond DB-1 fused silica capillary column (30 m$\times$0.25 mm i.d., 0.25 μm film thickness) from J & W Scientific, Inc. (Rancho Cordova, Calif.). The GC/MS is operated under standard autotune conditions with an injection port temperature of 250° C. and a column head pressure of 15 psi. The capillary column is equilibrated at 80° C., and approximately 1.0 min. after sample injection is increased to 300° C. at a rate of 30° C./min.

Data are collected from 6.0 to 7.5 min using the selected ion monitoring mode. The following [M-57]+ ions are monitored using a 10 ms dwell time for each: MMA, m/z 289.2; [methyl-$^2H_3$]-MMA, m/z 292.2; succinic acid, m/z 289.2; [1,4-$^{13}C_2$]succinic acid, m/z 291.2. MMA is quantitated by dividing the integrated area of the m/z 289.2 peak that elutes at approximately 6.8 min (the exact elution times are determined employing standards) by the integrated area of the m/z 292.2 peak that elutes at the same time, and then multiplying by the amount of [methyl-$^2H_3$] MMA standard (typically 100–200 ng) added to each sample. Succinic acid is quantitated in the same manner utilizing the m/z 289.2 and m/z 291.2 peaks that elute at approximately 7.2 min and multiplying by the amount of [1,4-$^{13}C_3$]succinic acid standard added to each sample (typically 1000–2000 ng). The integrated areas of the peaks for the internal standards, i.e. the m/z 292.2 and m/z 291.2 peaks eluting at about 6.8 and 7.2 min, respectively, are corrected for the amounts contributed to them by endogenous MMA and succinic acid as a result of naturally occurring isotope abundance. These corrections, which were determined for unenriched methylmalonic and succinic acids are as follows: (1) the m/z 292.2 peak from MMA (eluting at about 6.8 min) is approximately 1.9% of the MMA m/z 289.2 peak and (2) the m/z 291.2 peak from succinic acid (eluting at about 7.2 min) is approximately 10.8% of the area of the succinic acid m/z 289.2 peak.

The molecular weight of methylmalonic and succinic acid is 118. The molecular weight of a particular t-butyldimethylsilyl derivative is equal to the molecular weight of the dicarboxylic acid plus 228 (two t-butyldimethylsilyl groups). Molecular ion peaks, [M]+, representing the entire derivative were not observed. The major peak observed, representing 35–45% of the sum of all peaks observed in the m/z range of 100–400, in each case was the [M-57]+ fragment due to loss of $C_4H_9$. Smaller peaks, about 3–6% of the amount of the [M-56]+ peaks, at [M-15]+ due to the loss of a $CH_3$ group were also observed.

The capillary column employed in the GC/MS separation gave a complete separation for the derivatives having the same molecular weight, i.e., the derivatives of MMA and succinic acid were completely separated.

The method of this example has been employed for the assay of MMA in CSF as described in Allen et al., U.S. patent application Ser. No. 333,124, filed Apr. 3, 1989.

Samples of human serum, urine and other body fluids, such as CSF, appeared to contain no substances, as examined by GC/MS, that might interfere with the use of [methyl-$^2H_3$]methylmalonic and [14-$^{13}C_2$]succinic acids as internal standards for quantitation in the GC/MS procedure.

Methylmalonic and succinic were purchased from Sigma Chemical Company (St. Louis, Mo.). [Methyl-$^2H_3$]MMA (>99%, via custom synthesis) and [1,4-$^{13}C_2$]succinic acid (>99%) were purchased from Merck Sharpe & Dohme Isotopes (Montreal, Canada). [Methyl-$^4$C]MMA (via custom synthesis) and [1,4-$^{14}$C$_2$]succinic acid were purchased from New England Nuclear Corp. (Boston, Mass.).

EXAMPLE 3

Representative Improved Assay for MMA in serum (II)

Add 50 μl of an aqueous solution containing a known amount of internal standard, i.e. 100–200 ng of [methyl-$^2$H$_3$]MMA and 1,000–2,000 ng of [1,4-$^{13}$C$_2$]succinic acid, to a 400 μl sample and vortex. If less than 400 μl of sample is used, the volumetric difference is made up with 0.15M NaCl. A volume of 1 ml of water is added to the sample and the mixture is vortexed. The sample is then applied to an anion exchange column prepared as follows: introduce 0.2 ml of AGMP-1 resin 50–100 mesh (chloride form) (BioRad, Richmond, Calif.) to a disposable polypropylene column and wash the column with about 1.5 ml of H$_2$O. Care should be taken to minimize disturbing the column bed when the sample is applied. After the sample is applied, the column is washed sequentially with 2×3 ml of H$_2$O and 3 ml of methanol. Finally the column is washed with 3×3 ml of 0.01N acetic acid in methanol (prepared by adding 0.456 ml of concentrated glacial acetic acid to 800 ml methanol). This acetic acid wash is important as it removes components which interfere with the later quantitation of MMA derivatives by GC/MS. The sample is then eluted from the column with 2×0.6 ml of 1N HCl in methanol (prepared by mixing 8.83 ml of concentrated HCl (36.5–38%) and 91.3 ml of methanol). The eluants are collected and the solvent removed to dryness in a drying centrifuge (about 1½ hours). The sample residue is taken up in 300 μl 4N N$_4$OH in methanol and the sample is vortexed for 5 min. The sample is transferred to an autosampler vial and dried in a drying centrifuge (approximately 2 hrs). The dried samples are derivatized using acetonitrile/MTBSTFA mixture (20 μl acetonitrile+10 μl MTBSTFA). The derivatized sample vials are capped and the vials vortexed. The sample is then placed at 40° C. for at least 30 min. After removal from the oven, the samples are vortexed and analyzed for MMA, as described in Example 2. Derivatized samples can be analyzed within several days or may be stored at −20° C. for later assay.

EXAMPLE 4

Representative Combined Method for GC/MS Assay of MMA and Total Homocysteine in Serum This method combines the procedures described in Examples 1 and 3.

A volume of 50 μl containing a known amount of internal standards for MMA and homocysteine is mixed with a 400 μl sample of serum. If less than 400 μl of sample is employed, the difference is made up with 0.15M NaCl. Water (1 ml) is added to the sample and the mixture vortexed (5 sec.) A portion of about 150 μl of the sample is removed and mixed with 42.8 μl of an H$_3$BO$_3$-DTT mixture, prepared by mixing 50 μl of 0.5M H$_3$BO$_3$, pH 10, with 250 μl of 20 mg/ml DTT. The remaining portion of the sample (MMA assay sample, about 1.3 ml) is applied to an anion exchange column as described in Example 3. From this point the MMA samples are prepared as described in Example 3.

The homocysteine sample vial containing the DTT solution is covered with parafilm, vortexed for 5 sec. and placed at 40° C. for 30 min. The alkylating agent, iodoacetamide (57 μl of a 62.5 mg/ml solution in water) is added to each sample. The samples vials are covered with parafilm, vortexed for 5 sec., and placed at 40° C. for 30 min. A volume of 1 ml of H$_2$O is added to the sample and the mixture is vortexed for 5 sec. The entire sample is applied to the cation exchange column as described in Example 1. After the sample is applied, the column is washed sequentially with 3×3 ml of H$_2$O and 3 ml of methanol. The sample is eluted with 2×0.5 ml 4N NH$_4$OH in methanol, the eluates collected and the solvents removed in a drying centrifuge to complete dryness (about 1½ hrs.) The homocysteine samples should be dried in separate centrifuges from the MMA samples. The Hcys sample residue is taken up in 300 μl methanol vortexed 5 min. and transferred to an autosampler vial.

The samples are dried overnight in a drying centrifuge. The dried Hcys samples are derivatized with MTBSTFA and analyzed by SIM GC/MS for Hcys as described in Example 1.

EXAMPLE 5

Combined method for GC/MS assay of serum MMA, total homocysteine and creatine/creatinine Samples are prepared and treated as described in Example 4, except that the mixture of 50 μl aqueous internal standard solution also contains a known amount of creatine/creatinine internal standard, i.e. 4–5 μg of [methyl-$^2$H$_3$] creatine. Creatine/creatinine is quantitated in the same sample as Hcys. Creatine/creatinine samples are thus purified and derivatized as described for Hcys samples.

The GC/MS was operated as described in Examples 1 and 4 for analysis of Hcys samples. Combined creatine/creatinine concentrations in the samples were determined by monitoring the following ions using a 10 msec. dwell time for each: creatine/creatinine, m/z 298.2 and the corresponding fragment for [methyl-$^2$H$_3$] creatine/creatinine, m/z 301.2. Total combined creatine/creatinine was quantitated by dividing the integrated area of the m/z 298 peak that eluted at about 5.7 min. by the integrated area of the m/z 301 peak that eluted at the same time and then multiplying by the amount of creatine/creatinine internal standard added to samples. Peak areas were corrected for any contributions due to natural isotope abundance in the endogenous creatine/creatinine.

Test samples containing only creatine or creatinine which are treated, purified, derivatized and chromatographed, as described above have the same chromatograph with a major peak at 5.7 min. due to derivatized forms of creatine/creatinine. The creatine present in the samples is believed to be quantitatively converted under the basic conditions of sample preparation to creatinine. The assay thus measures creatine/creatinine as derivatized creatinine. The peak eluting at approximately 5.7 min. is believed to be creatinine derivatized with two silyl groups. The origin and structure of the m/z 298.2 (M-43)+ peak is unknown.

It will be appreciated by those skilled in the art that functionally equivalent alternatives exist for certain materials, techniques and procedures employed in the methods specifically described herein. Persons skilled in the art are able to select and use appropriate alternatives to achieve the desired results, as they are described herein. Any such alternatives now available to the art or that in the future become available to the art are considered to be within the spirit and scope of this invention.

We claim:

1. In a gas chromatography/mass spectrometry method for assaying a sample of a body fluid for the presence and concentration of one or more different endogenous sulfhydryl amino acid species comprising the steps:
   a. adding an internal reference standard sulfhydryl amino acid for each of said amino acid species to be assayed;
   b. adding reducing agent to said sample to insure randomization of said added internal reference sulfhydryl amino acids or the endogenous sulfhydryl amino acids present in said sample;
   c. partially purifying said sulfhydryl amino acids in said sample;
   d. derivatizing said reference sulfhydryl amino acids and said endogenous sulfhydryl amino acids in said sample:
   e. analyzing said sample in a gas chromatography/mass spectrometer to determine the presence and concentration of endogenous sulfhydryl amino acid present in said sample;
   wherein the improvement comprises one or both of the steps: treating said samples, between steps b and c, with iodacetamide to insure that the sulfhydryl amino acids present do not recombine with each other and partially purifying said samples at step c in a single ion exchange chromatographic extraction.

2. The method according to claim 1 wherein said sulfhydryl amino acid is homocysteine.

3. The method according to claim 1 wherein said ion exchange extraction is cation exchange extraction.

4. The method according to claim 3 wherein said cation exchange extraction employs a cation exchange resin in the hydrogen or ammonium ion form and wherein the sample is eluted with a solution of base in methanol.

5. The method according to claim 1 wherein said ion exchange extraction is an anion exchange extraction.

6. The method according to claim 5 wherein said anion exchange extraction employs an anion exchange resin in the hydroxide or acetate ion form and wherein the sample is eluted with a solution of acid in methanol.

7. The method according to claim 1 wherein said sulfhydryl amino acids are derivatized to silyl derivatives.

8. The method according to claim 7 wherein said samples are derivatized by addition of N-methyl-N-(t-butyldimethylsilyl)trifluoroacetamide.

9. The method according to claim 1 wherein said body fluid is serum or plasma.

10. The method of claim 1 which further comprises simultaneously assaying said samples for combined endogenous creatine and creatinine by:
    i. adding an internal reference standard for creatine and creatinine to said samples at step a;
    ii. treating said samples as in steps b–d;
    iii. in step e, analyzing said sample in a gas chromatograph/mass spectrometer to determine the amount of endogenous sulfhydryl amino acid, creatine and creatinine present in said sample.

11. The method according to claim 10 wherein said sulfhydryl amino acid is homocysteine.

12. The method according to claim 11 wherein said samples are derivatized by addition of N-methyl-N-(t-butyldimethylsilyl)trifluoroacetamide.

13. A gas chromatography/mass spectrometry method for the combined assay of a sample of a body fluid for the presence and concentration of one or more different endogenous sulfhydryl amino acid species and endogenous methylmalonic acid which comprises the steps:
    a. adding an internal reference standard sulfhydryl amino acid for each of said amino acid species to be assayed and adding an internal reference standard for methylmalonic acid;
    b. separating said sample into two portions: a first portion for assay of sulfhydryl amino acids and a second portion for assay of methylmalonic acid;
    c. adding reducing agent to said first sample portion to insure randomization of said added internal reference sulfhydryl amino acids or the endogenous sulfhydryl amino acids present in said first sample portion;
    d. treating said first sample portion with iodacetanide to insure that the sulfhydryl amino acids present do not recombine with each other;
    e. partially purifying said alkylated first sample portion of step (c) or (d) on a cation exchange column by elution with a solution of base in methanol;
    f. derivatizing said sulfhydryl amino acids and said endogenous sulfhydryl amino acids in said first sample portion;
    g. partially purifying said second sample portion employing a single step of anion exchange column chromatography;
    h. derivatizing said internal reference and said methylmalonic acid in said second sample portion; and
    i analyzing said first and second sample portions in a gas chromatograph/mass spectrometer to determine the presence and concentration of endogenous sulfhydryl amino acid and methylmalonic acid present in said sample.

14. The method according to claim 13 wherein said sulfhydryl amino acid is homocysteine.

15. The method according to claim 13 wherein said sample portions in steps f and h are derivatized by addition of N-methyl-N-(t-butyldimethylsilyl)-trifluoroacetamide.

16. The method of claim 13 wherein the purification of step g comprises applying said sample to an anion exchange column, washing said column containing said sample sequentially with water, methanol and a solution of about 0.01 to 0.1N acetic acid in methanol and eluting said sample from said column with a solution of about 0.1 to 1.0N HCl in methanol.

17. The method of claim 13 wherein said body fluid is serum or plasma.

18. The method of claim 13 which further comprises simultaneously assaying said samples for endogenous combined creatine and creatinine by:
    i. adding an internal reference standard for creatine and creatinine to said samples at step a;
    ii. treating said samples as in steps b–h; and
    iii. in step i, additionally analyzing said first sample portions in a gas chromatograph/mass spectrometer to determine sthe amount of endogenous combined creatine and creatinine present in said first sample portion.

19. The method of claim 18 wherein said sulfhydryl amino acid is homocysteine.

20. An improved method for detecting a deficiency of cobalamin or folate in humans and distinguishing therebetween by assaying body fluids for the presence of elevated levels of total endogenous homocysteine and endogenous methylmalonic acid wherein the improvement is the use of the combined assay method of claim 13.

21. The method according to claim 20 wherein said body fluid is serum or plasma.

22. The method of claim 20 wherein said body fluids are simultaneously assayed for endogenous combined creatine and creatinine, in addition to homocysteine and methylmalonic acid by:
   i. adding an internal reference standard for creatine and creatinine to said samples at step a;
   ii. treating said samples as in steps b–h; and
   iii. in step i, additionally analyzing said first sample portions in a gas chromatograph/mass spectrometer to determine the amount of endogenous combined creatine and creatinine present in said first sample portion.

* * * * *

UNITED STATES PATENT AND TRADEMARK OFFICE
CERTIFICATE OF CORRECTION

PATENT NO. : 5,438,017
DATED : August 1, 1995
INVENTOR(S) : Allen et al.

It is certified that error appears in the above-indentified patent and that said Letters Patent is hereby corrected as shown below:

On the Title page, item [57] Abstract, insert --is-- between "fluids" and "provided".

In column 2, line 15, replace "*clin.*" with --*Clin.*--.

In column 2, line 41, delete "a." preceding "(1986)".

In column 9, line 42, delete "% 9" and replace with --9%--.

In column 10, line 40, delete "subsequential" and replace with --subsequently--.

In column 10, line 68, delete "simultaneous," and replace with --simultaneously--.

In column 11, line 2, delete the period and replace with a colon. Insert the following chemical structure:

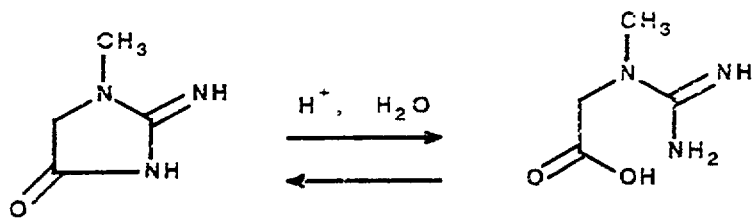

UNITED STATES PATENT AND TRADEMARK OFFICE
CERTIFICATE OF CORRECTION

PATENT NO. : 5,438,017
DATED : Aug. 1, 1995
INVENTOR(S) : Allen et al.

It is certified that error appears in the above-indentified patent and that said Letters Patent is hereby corrected as shown below:

In column 11, line 35, delete the hyphen at the end of the line.

In column 11, line 59, insert --and-- between "$H_2O$" and "vortexed.".

In column 12, line 40, delete "10" and replace with --1.0--.

In column 12, line 40, insert --the temperature-- between "injection" and "increased".

In column 13, line 46, delete "70-23" and replace with --70-230--.

In column 13, line 47, delete "0mesh" and replace with --mesh--.

In column 14, line 65, insert --acid-- between "succinic" and "were".

In column 15, line 29, delete "IN" and replace with --1N--.

In column 17, line 20 of claim 1, subparagraph d., delete ":" and insert --;--.

In column 17, line 21 of claim 1, subparagraph e., delete "chromatography" and replace with --chromatograph--.

In column 17, line 25 of claim 1, delete "wherein the improvement comprises" and replace with --the improvement comprising--.

UNITED STATES PATENT AND TRADEMARK OFFICE
CERTIFICATE OF CORRECTION

PATENT NO. : 5,438,017
DATED : Aug. 1, 1995
INVENTOR(S) : Allen et al.

It is certified that error appears in the above-indentified patent and that said Letters Patent is hereby corrected as shown below:

In column 18, line 19 of claim 13, subparagraph d., insert --optionally-- before "treating" and delete "iodacetanide" and replace with --iodacetamide--.

In column 18, line 22 of claim 13, subparagraph e., delete "alkylated".

In column 18, line 34 of claim 13, insert a period following the "I" at the beginning of the line so as to denote a subparagraph heading.

In column 18, line 62 of claim 18, subparagraph iii., delete "sthe" and replace with --the--.

Signed and Sealed this

Twentieth Day of February, 1996

Attest:

BRUCE LEHMAN

Attesting Officer       Commissioner of Patents and Trademarks